United States Patent
Gammersbach et al.

(10) Patent No.: US 6,632,972 B2
(45) Date of Patent: Oct. 14, 2003

(54) PROCESS FOR THE SELECTIVE PREPARATION OF DIB FROM AN I-BUTENE-CONTAINING $C_4$ STREAM

(75) Inventors: Alexander Gammersbach, Neuss (DE); Axel Gohrt, Cologne (DE); Joachim Grub, Dormagen (DE); Stefan Kaminsky, Dormagen (DE); Hans-Joachim Kramer, Dormagen (DE)

(73) Assignee: BP Koln GmbH, Cologne (DE)

( * ) Notice: Subject to any disclaimer, the term of this patent is extended or adjusted under 35 U.S.C. 154(b) by 0 days.

(21) Appl. No.: 09/930,267

(22) Filed: Aug. 16, 2001

(65) Prior Publication Data

US 2002/0045786 A1 Apr. 18, 2002

(30) Foreign Application Priority Data

Aug. 29, 2000 (DE) .......................... 100 42 280
Jan. 29, 2001 (DE) .......................... 101 03 834

(51) Int. Cl.[7] .............................. C07C 2/06; C07C 2/08; C07C 2/10; C07C 2/12; C07C 1/14
(52) U.S. Cl. ..................... 585/329; 585/326; 585/327
(58) Field of Search ................... 585/326, 327, 585/329

(56) References Cited

U.S. PATENT DOCUMENTS 3,256,351 A    6/1966   Leib
4,242,530 A  * 12/1980   Smith, Jr. .................... 585/510
5,789,643 A  *  8/1998   Herwig et al. ............... 585/314
5,877,372 A     3/1999   Evans et al. ................. 585/510

FOREIGN PATENT DOCUMENTS

| DE | 196 46 405 A1 | 5/1998 |
| EP | 0 008 860     | 3/1980 |
| EP | 0 850 904     | 7/1998 |
| EP | 0 950 433 A1  | 10/1999 |

OTHER PUBLICATIONS

Olah et al, "Oligomerization and Polymerization," Hydrocarbon Chemistry, pp. 525–527.

* cited by examiner

Primary Examiner—Thuan D. Dang
(74) Attorney, Agent, or Firm—Nixon & Vanderhye

(57) ABSTRACT

The invention relates to a process for preparing diisobutylene (DIB) from an i-butene-containing $C_4$ raffinate I, in which the $C_4$ stream is passed through a first hydroisomerization reactor (A) and a fractionation column (B) and is thus largely freed of 1-butene and 2-butene. It is subsequently dimerized over an acidic catalyst installed in a reactive column (E). The feed stream to this reactive column contains not only i-butene but also butanes which make the reaction temperature in the fixed bed controllable by removal of the heat of reaction. In the fractionation column (B), a side stream can be subjected to a further hydroisomerization in a reactor (C).

18 Claims, 1 Drawing Sheet

PROCESS FOR THE SELECTIVE PREPARATION OF DIB FROM AN I-BUTENE-CONTAINING C₄ STREAM

The present invention relates to a process for the selective dimerization of i-butene present in a $C_4$ raffinate I and comprises the steps of a first hydroisomerization of the raffinate I, a subsequent removal of 2-butene and n-butane by distillation in a column and the selective dimerization of part of the i-butene-containing product from the top of the column.

BACKGROUND OF THE INVENTION

The dimers of i-butene are 2,4,4-trimethyl-1-pentene and 2,4,4-trimethyl-2-pentene. They still each contain a double bond and can be passed to the oxo process or to esterification, for example to produce isononyl alcohol from diisobutylene (DIB) and then dinonyl phthalate or, in the case of direct esterification of the DIB, dioctyl phthalate which are used as plasticizers for thermoplastics. Triisobutene can also be processed to produce dodecyl mercaptan, a rubber auxiliary. Finally, mention may be made of the addition of DIB or octanes derived therefrom by hydrogenation to motor fuel.

It is already known that i-butene can be oligomerized over many electrophilic catalysts (Olah, Molaur, Hydrocarbon Chemistry, Wiley, 1995). For example, processes using acidic ion exchangers or pentasil zeolites have been described. A disadvantage of these methods is the low selectivity to DIB, since the processes always form not only the main product but also higher oligomers of i-butene, namely triisobutene ($C_{12}$), tetraisobutene ($C_{16}$), pentaisobutene ($C_{20}$) and so forth, whose proportions decrease further with ever increasing degree of oligomerization. Such a process has to be followed by a separation of the components formed.

If the feed stream contains not only i-butene but also 1-butene or 2-butene, the selectivity to DIB decreases further, since $C_8$ products are simultaneously formed from i-butene and 1-butene or 2-butene (known as codimers) at high conversions.

Owing to the close proximity of their boiling points to that of DIB, these cannot be separated off at justifiable cost and thus represent a loss source in the process.

For this reason, processes which have a very high selectivity to DIB are sought. One way of increasing the selectivity is high dilution of the i-butene by octanes and oxygen compounds as disclosed in U.S. Pat. No. 5,877,372. However, unreacted i-butene and inert substances have to be separated off and circulated in this process.

Another route is described by EP 0 008 860 A1, where the catalyst is installed in wire mesh pockets in a distillation column. In this process, raffinate I having an i-butene content of about 50% and a 1-butene content of 25% is processed at low pressures. Despite this, the codimers which are virtually impossible to separate off are the major by-products. In addition, low i-butene conversions and thus i-butene losses have to be accepted in this process.

EP 0 850 904 A1 describes the separation of 1-butene and 2-butene from i-butene in $C_4$ raffinate I by appropriately linking hydroisomerization reactors with various distillation columns. However, the object here is to isolate a very pure i-butene stream.

DE 196 46 405 A1 describes the selective oligomerization of i-butene from a 1-/2-butene-containing $C_4$ stream, with the particularly troublesome 1-butene being converted into 2-butene by hydroisomerization and the 2-butene being separated from the i-butene by distillation. The resulting i-butane/i-butene stream is oligomerized over a heterogeneous acid catalyst in a reactor. Virtually no codimers which are difficult to remove are formed, but $C_{12}$-oligomers constitute the main product.

SUMMARY OF THE INVENTION

In view of this background, it is an object of the present invention to improve the known processes so that DIB can be prepared in high conversions and with high selectivity from a stream comprising i-butene, 1-/2-butene and butanes.

This object is achieved by a process having the features specified in claim 1.

The process for preparing diisobutylene (DIB) from an i-butene-containing $C_4$ raffinate I comprises the steps a) subjecting the $C_4$ raffinate I to a first hydroisomerization over a noble metal catalyst, with this being carried out at 30–90° C., preferably 50–60° C., at 5–30 bar, preferably 10–20 bar, at an LHSV of 1–30 h$^{-1}$, preferably 5–30 h$^{-1}$, and using 3–20 standard liters of gaseous hydrogen per liter of liquid $C_4$raffinate I, which is above the amount of hydrogen required for the hydrogenation of highly unsaturated compounds in the $C_4$ raffinate I;

b) fractionally distilling the hydroisomerization product from a) in a fractionation column, with this being carried out at 5–25 bar, preferably 8–12 bar, and the temperature established under this pressure and 2-butene and n-butane being taken off as bottoms and i-butene and i-butane being taken off at the top;

c) optionally taking off a side stream from this fractionation column above the inlet, preferably at the level of the middle of the column, and subjecting it to a second hydroisomerization over a noble metal catalyst, with this hydroisomerization being carried out at 30–90° C., preferably 50–60° C., at 5–30 bar, preferably 10–20 bar, at an LHSV of 1–30 h$^{-1}$ and using 3–20 standard liters of gaseous hydrogen per liter of $C_4$ raffinate I and the hydroisomerization conditions in a) and c) being identical or different; with the hydroisomerization product being recirculated to the fractionation column used under b), preferably above the offtake point;

d) condensing the product from the top of the column in b), dividing it into two parts and subjecting the first part to a third hydroisomerization over a noble metal catalyst, with this hydroisomerization being carried out at 30–90° C., preferably 50–60° C., at 5–30 bar, preferably 10–20 bar, at an LHSV of 1–30 h$^{-1}$, preferably 5–30 h$^{-1}$, and using 0.3–20 standard liters of gaseous hydrogen per liter of condensate and the hydroisomerization conditions in a) and d) being identical or different and the hydroisomerization product from d) being recirculated to the fractionation column of b), preferably into its upper third;

e) introducing the second part of the condensed product from the top of the column in b) into a reactive column in which the $C_4$-hydrocarbons are vaporized preferably at 50–100° C. and are passed over an acidic heterogeneous catalyst over which the i-butene is dimerized, with the dimerization being carried out at 40–100° C., at 3–30 bar, preferably 5–20 bar, and an LHSV of 5–50 h$^{-1}$. The catalyst can be present in a special column packing, e.g. in a commercially available packing of the type MONTZ Multipak I which allows separation of the DIB from the feed stream. Thus, inert C$_4$-hydrocarbons can be condensed at the top of the reactive column, with part of this condensate being able to be recirculated to the column to remove the heat of reaction and the other part being able to be taken off, and dimerization products, i.e. C$_8$-hydrocarbons, being able to be taken off at the bottom of the reactive column.

In the process of the invention, the C$_4$ stream is thus largely freed of 1-butene and 2-butene and subsequently dimerized over an acidic catalyst installed in a reactive column. The feed stream to this reactive column contains butanes in addition to i-butene, which make the reaction temperature in the fixed bed controllable by removal of the heat of reaction. The process of the invention differs from the process known from DE 196 46 405 A1 in, in particular, the steps c) (optional) and e).

As i-butene-containing C$_4$ mixture, it is possible to use a C$_4$ raffinate I which is obtained from the crude C$_4$ distillation fraction of a cracker product by removing the 1,3-butadiene present therein by extraction and making economic use of it. This extraction also removes other highly unsaturated hydrocarbons, e.g. vinylacetylene, 1,2-butadiene and other acetylene compounds, from the crude C$_4$ distillation fraction. The C$_4$ raffinate I obtained after the extraction still contains minor amounts of highly unsaturated compounds. The predominant components of C$_4$ raffinate I are n-butane, i-butane, 1-butene, 2-butene (cis and trans) and i-butene. C$_3$- and C$_5$-hydrocarbons may also be present in minor amounts.

The first hydroisomerization as reaction step a) of the process of the invention is carried out at a temperature of 30–90° C., preferably 30–80° C., particularly preferably 40–60° C., and a pressure of 5–30 bar, preferably 10–20 bar. An LHSV (Liquid Hourly Space Velocity) of 1–30 h$^{-1}$, preferably 5–30 h$^{-1}$, particularly preferably 5–12 h$^{-1}$, is employed. The amounts of gaseous hydrogen added has to remove the abovementioned highly unsaturated compounds and also be present for the hydroisomerization. Partial hydrogenation of the highly unsaturated hydrocarbons forms monounsaturated hydrocarbons which are already present in the C$_4$ raffinate I. The amount of hydrogen necessary to eliminate the highly unsaturated hydrocarbons depends on the proportions in which they are present in the feed and can easily be determined by analytical methods known to those skilled in the art. The additional amount of hydrogen required above this amount is 2–15 standard liters, preferably 3–10 standard liters, of gaseous hydrogen per liter of liquid raffinate I.

For the hydroisomerization, C$_4$ raffinate I is in the liquid state. It can be passed over the catalyst from the top downwards in the trickle mode, or the catalyst-containing reactor is supplied from the bottom upwards in the flooded mode. The gaseous hydrogen can be conveyed in cocurrent or in countercurrent to the C$_4$ raffinate I. The reactor is preferably operated in the flooded mode and the hydrogen is preferably passed through it in cocurrent.

All noble metal hydrogenation catalysts are suitable for the hydroisomerization. Possible noble metals are Ru, Rh, Pd, Ir, Pt, preferably Ru, Pd, Pt, particularly preferably Pd. As support materials to which the noble metals may be applied, it is possible to use Al$_2$O$_3$ in various modifications, SiO$_2$, carbon, kieselguhr, BaSO$_4$ and other salts. It has been found to be useful to regulate the activity of the noble metals of the abovementioned type by addition of sulphur compounds.

In reaction step b) of the process of the invention, the hydroisomerization product from a), which now comprises i-butene and 2-butene as main components, is fractionally distilled. This is carried out at a pressure of 5–25 bar and the temperatures established under the distillation conditions. Typically, at a particularly preferred column pressure of 11 bar, the temperature established at the top of the column is 73° C. and that established at the bottom of the column is 78° C. It is also preferred that the reaction steps a), b), c) and d) of the process of the invention are carried out at the same pressure, and the temperatures are in each case matched to requirements.

Above the point at which the hydroisomerization product is fed into the distillation column a substream of the product is preferably taken from the column and, in step c), subjected to a second hydroisomerization in a side stream reactor. As in the first hydroisomerization step, preference is given to using an LHSV of 1–30 h$^{-1}$, particularly preferably 5–25 h$^{-1}$. The liquid can be passed through the reactor from the top downward or preferably from the bottom upward in the second hydroisomerization step too, with the hydrogen likewise being able to be conveyed in cocurrent or in countercurrent. The amount of hydrogen introduced can be lower than in the first hydroisomerization, since diene compounds no longer have to be expected in the second reactor. The product is returned to the column immediately above the offtake point. The 2-butene formed in the second hydroisomerization step goes to the bottom of the column. Offtake and reintroduction of product from/to this second hydroisomerization are preferably carried out at the half height of the distillation column described under b).

The bottom product obtained from reaction step b) is a mixture of mainly n-butane and 2-butene. The amount of 2-butene is made up of the 2-butene originally present in the C$_4$ raffinate I and the 2-butene formed by hydroisomerization of 1-butene.

The product taken off at the top of the distillation b) of the process of the invention consists essentially of i-butene and i-butane and minor amounts of 1-butene. It is condensed and then divided into two parts. The first part is, in reaction step d), fed to a third hydroisomerization which is likewise carried out under the conditions specified for the first and second hydroisomerizations.

The ratio of the two substreams of the condensed product from the top of the fractionation column is set so that 10–50 parts by volume, preferably 25–35 parts by volume, are fed as first part to the third hydroisomerization d), based on 1 part by volume fed as the second part to the dimerization described under e). Since this second part together with the bottoms from the fractionation column correspond to the total volume of C$_4$ raffinate I fed to the first hydroisomerization, the flow of material through the process of the invention has superposed on it a circulation through the second and third hydroisomerization reactors and the fractionation column which corresponds in the above-described way to 10–50 times the substream fed to the dimerization.

In reaction step e) of the process of the invention, the second part of the condensed product from the top of the column is fed to the dimerization in a reactive column. As catalysts for the dimerization, use is made of heterogeneous, inorganic or organic catalysts, for example acidic zeolites, silica gels and acidic Al$_2$O$_3$, acidic sheet silicates and framework silicates, acid-doped support materials or gel-like or macroporous cation exchangers in the H$^+$ form. The catalyst is present in a packing, and the $C_4$ fraction is passed in gaseous form through the catalyst packing at temperatures of from 40 to 100° C. The i-butene dimerizes over the catalyst, the inert butanes condense at the top of the column and are returned as runback. This runback comprising inert $C_4$-hydrocarbons keeps the temperature over the catalyst constant by the heat of reaction being removed by vaporization of the inert butanes.

DETAILED DESCRIPTION OF PREFERRED EMBODIMENTS

Figure 1:
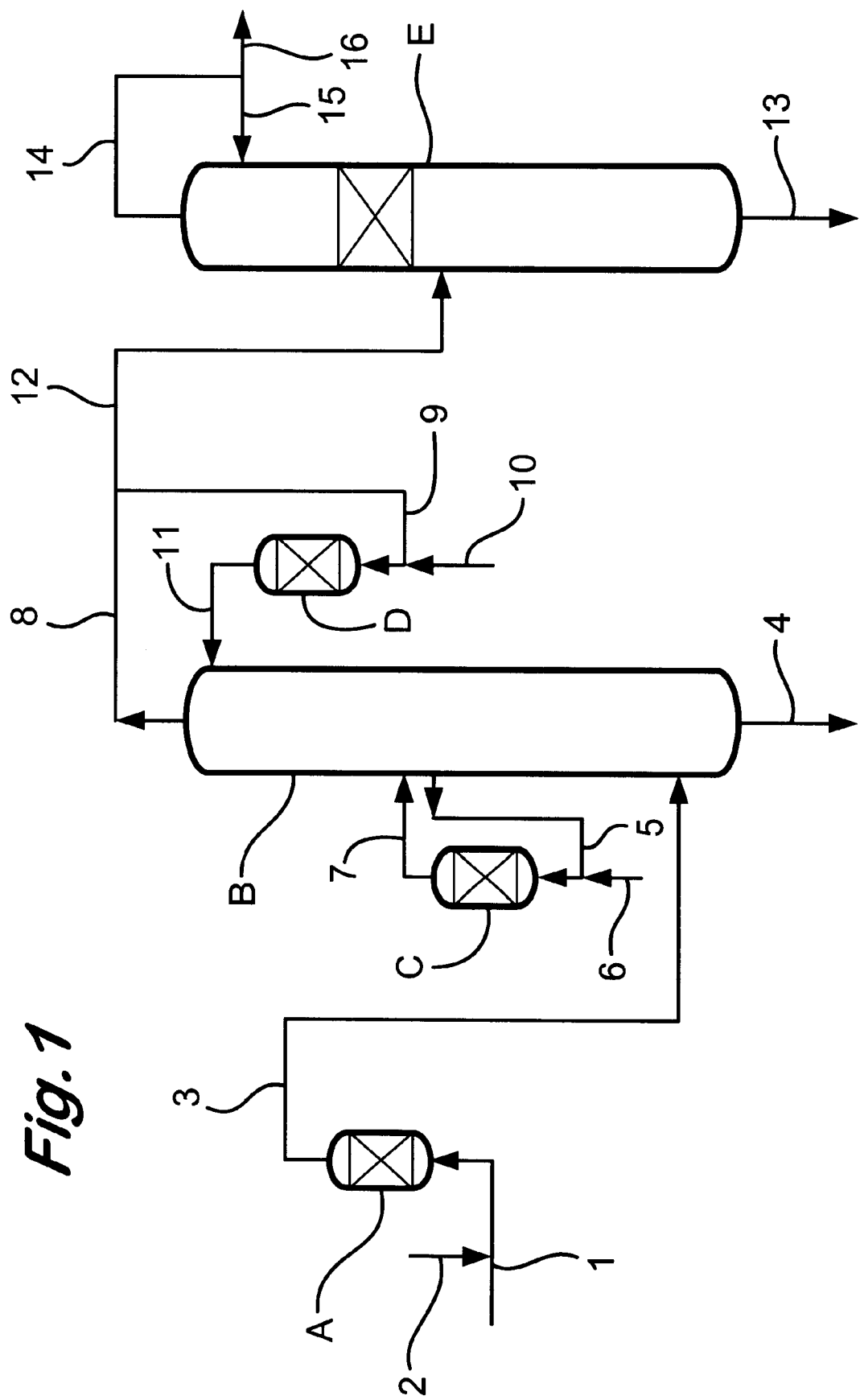
FIG. 1 shows, by way of example, an apparatus for carrying out the process of the invention.

Liquid $C_4$ raffinate I which is characterized by a content of i-butene to be dimerized is fed via line 1 to a first hydroisomerization reactor A which is provided with a fixed bed of noble metal hydrogenation catalyst. The required amount of $H_2$ is mixed into the $C_4$ raffinate I via line 2. A is in the flooded state and the reaction mixture is passed through it from the bottom upward. The first hydroisomerizate leaving A is conveyed via line 3 to the distillation column B (fractionation column) from which a mixture comprising essentially n-butane and 2-butene is taken off as bottom product 4.

A substream from column B, which comprises mainly n-butane, i-butene and 2-butene and also some 1-butene, is taken off via line 5, admixed with $H_2$ via line 6 and hydroisomerized a second time in the reactor C. The product stream from the reactor C is returned via line 7 to the column B. The offtake line 5 is preferably located at the middle of the column B, and the return line 7 preferably enters the column just above the offtake line 5.

The product taken from the top of the reactor B via line 8 comprises mainly i-butene and butanes together with small amounts of 1-butene and 2-butene. This stream is divided into two parts and the first part is fed via line 9 to a third hydroisomerization in the reactor D. $H_2$ is added via line 10. The product of this third hydroisomerization is conveyed via line 11 from the reactor D back into the column B.

The second part of the stream from the top of the column is conveyed via line 12 to the column E where dimerization is carried out. The proportion conveyed via line 9 is always greater than that conveyed via line 12. The acidic catalyst is present in a packing above the point at which line 12 enters the column E. The DIB and the by-products are taken off via line 13 at the bottom of the column E and may be separated by distillation. The inert $C_4$-hydrocarbons are condensed at the top of the column (line 14) and the major part is returned via line 15 to remove the heat of reaction. Excess inerts can be discharged via line 16.

EXAMPLES

Example 1a

Hydroisomerization of 1-butene to 2-butene

A hydroisomerization reactor which was connected like A in FIG. 1 to the further apparatuses shown in FIG. 1 was activated at 70° C. for 24 hours using 200 standard l/h of hydrogen. It was subsequently operated at 55° C. using 15 standard l/h of hydrogen and 1300 g/h of feed. The results listed in Table 1 were obtained:

TABLE 1

Results of the first hydroisomerization

|  | Feed/% by volume | Product/% by volume |
| --- | --- | --- |
| i-Butane | 1.6 | 1.7 |
| n-Butane | 9.0 | 11.0 |
| i-Butene | 45.6 | 44.8 |
| 1-Butene | 25.7 | 2.9 |
| 2-Butene (cis, trans) | 17.6 | 39.3 |
| 1,3-Butadiene | 0.2 | 0 |
| Total $C_{5+}$ | 0.2 | 0.2 |

Example 1b

Distillation

A distillation column having a length of 4 m and an internal diameter of 50 mm, filled with 6 mm wire mesh rings (number of theoretical plates: 48), which was connected like B to the further apparatuses shown in FIG. 1, was supplied continuously with 1297 g/h of hydroisomerized raffinate I. At a pressure of 11 bar, a temperature at the top of 68.5° C. and a temperature at the bottom of 77.8° C., 374 g/h of product from the top, 9650 g/h of runback and 923 g/h of bottoms were obtained.

Example 1c/d

Hydroisomerization

Above the product inlet into B, a substream is taken from the column and passed through a second hydroisomerization reactor which was connected like C to the further apparatuses shown in FIG. 1. The runback from Example 1b was, before being returned to the column B, passed through a further hydroisomerization reactor which was connected like D to the further apparatuses shown in FIG. 1. The following reaction conditions were set:

Reactor C: 1.425 l of catalyst, Pd on alumina (Procatalyse), activated as in Example 1a, 4400 g/h of feed, LHSV: 5 $h^{-1}$, temperature: 55° C., pressure: 11 bar, 35 l/h of $H_2$.

Reactor D: 0.715 l of catalyst, 9650 g/h of feed, LHSV: 22 $h^{-1}$, temperature: 52° C., pressure: 11 bar, 15 l/h of $H_2$. The product from the top corresponded to the composition of the feed in Example 1e.

Example 1e

Dimerization of the i-butene in the $C_4$ Stream According to the Invention

The reactive column which was connected like E in FIG. 1 to the further apparatuses shown in FIG. 1 was operated under the following conditions and gave the results listed in Table 2:

The catalyst used was 100 g of cation exchanger in the $H^+$ form.

In Experiment 1 (E1), 300 g of hydroisomerate according to the invention was fed in via line 12 as shown in FIG. 1 over a period of 60 minutes. The hydroisomerate according to the invention which was used had the composition shown in Table 2 (all figures in % by weight):

For comparison, the same amount of a hydroisomerate which was not according to the invention (comparison) was reacted without hydroisomerization. This feed stream had the composition shown in Table 2 (all figures in % by weight):

In Experiment E1 and in the comparative experiment, the pressure was 10 bar and the temperatures over the catalyst were from 65 to 80° C.

In Experiment E2, 250 g of the hydroisomerate according to the invention having the composition shown in Table 2 were fed in via line 12 in FIG. 1. For Experiment E2, the pressure was 6.5 bar and the temperature over the catalyst was 50° C.

TABLE 2

|  | E1 | E2 | Comparison |
|---|---|---|---|
| i-Butane | 19.5 | 13.3 | 2.0 |
| n-Butane | 2.2 | 0.7 | 10.2 |
| i-Butene | 77.3 | 85.5 | 45.4 |
| 1-Butene | 0.1 | 0.1 | 25.5 |
| 2-Butene (cis, trans) | 0.6 | 0.3 | 16.5 |
| High boilers | — | — | 0.1 |
| Butadiene | — | — | 0.1 |

TABLE 3

Results of the dimerization

|  | E1 | E2 | Comparison |
|---|---|---|---|
| Conversion of i-butene/% | 98.3 | 96.2 | 75.5 |
| Product distribution/residual $C_4$/% by weight | 21.9 | 14.0 | 55.8 |
| i-Butene content of the residual $C_4$/% by weight | 6.0 | 23.3 | 20.0 |
| DIB content of product/% by weight | 64.8 | 75.6 | 36.0 |
| Codimer content of product/% by weight | 0.4 | 0.2 | 4.6 |
| $C_{12}$ content of product/% by weight | 12.4 | 9.0 | 2.1 |
| $C_{16}$ content of product/% by weight | 0.5 | 1.0 | 0.4 |

What is claimed is:

1. Process for preparing diisobutylene (DIB) from an i-butene-containing $C_4$ raffinate I, comprising:

a) subjecting the $C_4$ raffinate I to a first hydroisomerization (A) over a noble metal catalyst, with this being carried out at 30–90° C., 5–30 bar, an LHSV of 1–30 $h^{-1}$ and using 3–20 standard liters of gaseous hydrogen per liter of liquid $C_4$ raffinate I, which is above the amount of hydrogen required for the hydrogenation of highly unsaturated compounds in the $C_4$ raffinate I;

b) fractionally distilling the hydroisomerization product from a) in a fractionation column (B), with this being carried out at 5–25 bar and the temperature established under this pressure and 2-butene and n-butane being taken off as bottoms (4) and i-butene and i-butane being taken off at the top (8);

c) optionally, taking a side stream (5, 7) from this fractionation column (B) and subjecting to a second hydroisomerization (C) over a noble metal catalyst, with this hydroisomerization being carried out at 30–90 ° C., at 5–30 bar, at an LHSV of 1–30 $h^{-1}$ and using 3–20 standard liters of gaseous hydrogen per liter of $C_4$ raffinate I and the hydroisomerization conditions in a) and c) being identical or different;

d) condensing the product from the top of the column in b), dividing into two parts and subjecting the first part to a third hydroisomerization (D) over a noble metal catalyst, with this hydroisomerization being carried out at 30–90° C., at 5–30 bar, at an LHSV of 1–30 $h^{-1}$, and using 0.3–20 standard liters of gaseous hydrogen per liter of condensate and the hydroisomerization conditions in a) and d) being identical or different and the hydroisomerization product from d) being recirculated to the fractionation column of b);

e) introducing the second part of the condensed product from the top of the column in b) into a reactive column in which the $C_4$-hydrocarbons are vaporized butanes are condensed, and returned to the reactive column, and are passed over an acidic heterogeneous catalyst, wherein iso-butene is dimerized.

2. Process according to claim 1, wherein step e) is carried out at a temperature of 50–100° C.

3. Process according to claim 1, wherein steps a), c) and/or d) are carried out at a temperature of 50–60° C.

4. Process according to claim 1, wherein steps a), c) and/or d) are carried out at a pressure of 10–20 bar.

5. Process according to claim 1, wherein steps a) and/or d) are carried out at an LHSV of 5–30 $h^{-1}$.

6. Process according to claim 1, wherein step b) is carried out at 8–12 bar.

7. Process according to claim 1 wherein the side stream from the fractionation column (B) is taken off above the inlet (3), at the level of the middle of the column, and the hydroisomerization product is recirculated to the fractionation column above the offtake point.

8. Process according to claim 1, wherein the hydroisomerization product from d) is recirculated to the fractionation column of b) in its upper third.

9. Process according to claim 1, wherein step e) the i-butene is dimerized over the catalyst.

10. Process according to claim 9, wherein the i-butene is dimerized over the catalyst at 40–100° C.

11. Process according to claim 8, wherein step e) is carried out at 3–30 bar.

12. Process according to claim 11, wherein step e) is carried out at 5–20 bar.

13. Process according to claim 8, wherein step e) is carried out at an LHSV of 5–50 $h^{-1}$.

14. Process according to claim 1, wherein the catalyst in step e) is present in a column packing.

15. Process according to claim 1, wherein inert $C_4$-hydrocarbons are condensed at the top of the reactive column (E) in step e), with part of this condensate being able to be recirculated to the column to remove the heat of reaction and the other part being able to be taken off.

16. Process according to claim 1, wherein in step e) dimerization products are taken off at the bottom (13) of the reactive column (E).

17. Process according to claim 1, wherein the catalysts used for the dimerization in step e) are heterogeneous, inorganic or organic catalysts.

18. Process according to claims 17, wherein the catalysts used for the dimerization in step e) are acidic zeolites, silica gels and acidic $Al_2O_3$, acidic sheet silicates and framework silicates, acid-doped support materials or gel or macroporous cation exchangers in the $H^+$ form.

* * * * *